United States Patent [19]
Schmidt-Ruppin

[11] Patent Number: 4,512,972
[45] Date of Patent: Apr. 23, 1985

[54] NASAL PREPARATION AND PROCESSES FOR THEIR PRODUCTION

[75] Inventor: Karl H. Schmidt-Ruppin, Arlesheim, Switzerland

[73] Assignee: Kureha Chemical Industry Co., Ltd., Tokyo, Japan

[21] Appl. No.: 295,934

[22] Filed: Aug. 24, 1981

Related U.S. Application Data

[63] Continuation of Ser. No. 164,642, Jun. 30, 1980, abandoned.

[51] Int. Cl.³ ............................................ A61K 39/145
[52] U.S. Cl. ...................................................... 424/89
[58] Field of Search .......................... 424/89, 171, 180

[56] References Cited

FOREIGN PATENT DOCUMENTS

| | | |
|---|---|---|
| 2553971 | 8/1976 | Fed. Rep. of Germany . |
| 2655844 | 7/1977 | Fed. Rep. of Germany . |
| 2816087 | 2/1978 | Fed. Rep. of Germany . |
| 2813353 | 10/1978 | Fed. Rep. of Germany . |
| 2081341 | 1/1975 | France . |
| 2293214 | 7/1976 | France . |
| 2312261 | 12/1976 | France . |
| 2385734 | 10/1978 | France . |
| 7308489 | 3/1973 | Japan . |
| 76036322 | 10/1976 | Japan . |
| 1521168 | 8/1976 | United Kingdom . |

OTHER PUBLICATIONS

Chem. Abstracts on Krestin-PSK 93:61434m 92:174521k, 51886A(1980) 91:32758y, 90:66773u(1979), 89:213509x(1978), 87:100680m, 145600B, 177718n(1977), 86:25880A(1977), 86:118972z(1977), 84:130282p(1976), 82:119037A(1975), 84:54002e(1976), 85:17132x(1976), 85:25740(1976).
Kureha Chemical Industry Co., Ltd. "Outline of PSK" 45 pp.
Hiraset et al. Yakubaku Zasshi 96(4): 413–418, (1976).

Primary Examiner—Shep K. Rose
Attorney, Agent, or Firm—Oblon, Fisher, Spivak, McClelland & Maier

[57] ABSTRACT

The present invention relates to nasal preparations which contain, as active ingredient, one or more nitrogen-containing polysaccharides obtained from fungi, in particular the polysaccharide krestin, and which exert a prophylactic action lasting several days against infections caused by viruses of the respiratory tract, especially influenza A and B viruses, as well as vaccine nasal preparations which contain the above mentioned active ingredient together with viruses of the respiratory tract of at least one strain and which impart a long-term protective action on single administration. The invention is also concerned with the production and use of these nasal preparations.

8 Claims, No Drawings

NASAL PREPARATION AND PROCESSES FOR THEIR PRODUCTION

This is a continuation of application Ser. No. 164,642 filed on June 30, 1980 now abandoned.

The present invention relates to novel nasal preparations for the prevention of infections caused by viruses of the respiratory tract, especially by influenza viruses A and B, processes for the production of these preparations and the use thereof.

Surprisingly, it has been found that nitrogen-containing polysaccharides obtained from fungi, in particular the nitrogen-containing polysaccharide krestin discussed in more detail below, have a prophylactic action lasting several days against viruses of the respiratory tract, especially influenza A and B viruses, when applied intranasally, and, when mixed with viruses of the respiratory tract, neutralises the infectivity of the viruses in question without impairing their capacity to stimulate antibody formation.

Accordingly, it is an object of the present invention to provide nasal preparations for the prevention of infections caused by viruses of the respiratory tract, said preparations containing, as active ingredient, one or more nitrogen-containing polysaccharides obtained from fungi. The preparations of this invention are in particular conventional medicinal formulations for intranasal application.

The nitrogen-containing polysaccharide krestin, also known as PSK, was obtained by research workers of the Kureha Chemical Co. Ltd., Tokyo, by extraction from myzelia of fungi of the genus Coriolus, in particular from Coriolus versicolor (Fr.) Qel (Basidiomycetes, family of the Polyporaceae), at elevated temperature with water, after there were grounds for supposing that myzelia contained tumour-inhibiting substances.

The extraction of a nitrogen-containing polysaccharide mixture has been described in Japanese patent publication 75/36322 (filed on 3.10.68), and the fractionation of the extracts with barium hydroxide to isolate the components active against Sarcoma 180 is described in Japanese patent publication 73/8489 (filed on 29.9.70). Further patent applications claiming the Japanese priority of 18.12.75, such as German Offenlegungsschrift 2 655 844, relate to a modified method of extraction. Detailed particulars on the fractionation of the crude extracts and isolation of the tumour-inhibiting fractions, as well as on the nature and amount of the sugar and amino acids obtained by hydrolysis of the different fractions, are provided by Susumi Hirase et al. in Yakugi Zasshi (J. Pharm. Soc. Japan) 96, 413–418 (1976). According to the subsequent publication [ibid. 96, 419–424 (1976)], the same authors investigated the constitution of the $\beta$-D-glucane components of the fractionated polysaccharides. Shigeru Tsukagoshi et al. have reported on the growth-inhibiting action of PSK on the sarcoma 180 in mice and the ascites-hepatome AH-13 in oral administration in the periodical Gann 1974, 65(6) 557–8 [CA. 82, 119037a (1975)], and in Prog. Chemother., Proc. 8th Int. Congr. Chemother., 1973 [CA. 84, 54002e (1976)]. Chemical, and especially pharmacological and clinical, publications and reports on the tumour-inhibiting, nitrogen-containing polysaccharide referred to herein as PSK, are summarised and discussed in the in-house publication "An Outline of PSK", 1977, of the Kureha Chemical Industries Co. Ltd., Tokyo. According to this publication, PSK is a brown or brownish tasteless powder with a faint specific odour, sparingly soluble in methanol, pyridine, chloroform, benzene and hexane, but soluble in water. A 1% aqueous solution is brownish with slight turbidity, and its pH value is around 6.6 to 7.2. PSK (krestin) decomposes when heated to temperatures above 120° C. The prophylactic action against viruses of the respiratory tract can vary within certain limits according to the different lots of krestin produced and sold by the Kureha Chemical Co. Ltd. for use as tumour-inhibiting substance. For this reason it is advisable to test in advance samples of the lots to be used by means of assays on mice for affording protection against infection and, if necessary, to refrain from using individual lots with lower activity, e.g. an activity which is evidently lower than that of the lots employed for the assays described hereinbelow.

The prophylactic action of krestin against infections caused by influenza viruses A and B are apparent from e.g. the assays described hereinbelow. The krestin used for all assays was taken from the lots designated and sold by the Kureha Chemical Co. Ltd. as Lots 1228 and 1214, both of which are recognised as having good prophylactic action against influenza viruses.

METHOD

Male NMRI mice having a body weight of 16–18 g and divided into groups of 10 are slightly anaesthetised with ether and infected intranasally with a suspension of influenza A/Hong Kong 1/68 virus ($H_3N_2$) and influenza B/Ann Arbor virus in 0.05 ml of water. The suspension is fatal to 90% of the animals. The mice in the different groups, except those in the two control groups, are treated beforehand once or repeatedly by intranasal application of 0.05 ml of solutions of krestin in different concentrations in distilled water and at the times indicated in Table 1. The effect of the prophylactic treatments is determined from the percentage of mice surviving after 15 days in comparison to the control groups, and from the prolongation of the average survival time within an observation period of 15 days in comparison to the control groups. The results are reported in Table 1.

| | Application time in days (D) or mins. (M) before infection | Protective action against influenza viruses | | | |
|---|---|---|---|---|---|
| $C^1$ | | A Hong Kong 1/68 survivors (%), test/contr. | average survival time (%) test/contr. | B/Ann Arbor survivors (%) test/contr. | average survival time (%) test/contr. |
| 40 | D5,D3,M30 | 80/10** | 13.3/8.8** | 80/10** | 13.6/8.7*** |
| 10 | D5,D3,M30 | 80/10** | 13.3/8.8** | 70/10* | 12.9/8.7** |
| 10 | D3,M30 | 89/10** | 14.4/8.8*** | 70/10* | 13.5/10.5*** |
| 10 | M30 | 50/10 | 11.5/9.8 | 20/10 | 10.4/10.5 |
| 10 | D1 | 40/10 | 11.9/9.8 | 20/10 | 11.1/10.5 |
| 10 | D2 | 70/10 | 12.6/9.7 | | |
| 10 | D3 | 80/10** | 13.7/9.8*** | 50/10 | 12.5/10.5** |

-continued

| | | Protective action against influenza viruses | | | |
|---|---|---|---|---|---|
| $C^1$ | Application time in days (D) or mins. (M) before infection | A Hong Kong 1/68 survivors (%), test/contr. | average survival time (%) test/contr. | B/Ann Arbor survivors (%) test/contr. | average survival time (%) test/contr. |
| 10 | D4 | 80/10** | 13.7/9.7*** | | |
| 10 | D7 | 80/10** | 14.0/9.7*** | | |
| 10 | D9 | 70/10* | 13.2/9.7*** | | |
| 10 | D11,D9,D7,D4,D2 | 90/10** | 14.2/9.7** | | |
| 4 | D3,M30 | 30/10 | 10.9/9.8 | 60/10 | 13.1/10.5** |
| 1 | D3,M30 | 20/10 | 9.4/9.8 | 50/10 | 12.7/10.5 |

*significant $P<0.05$
**significant $P<0.05$
***significant $P<0.001$
[1] concentration of the solution in mg/ml
contingency test for survivors and Cox test for average survival time It is evident from the results reported in Table 1 that krestin at a concentration of 10 mg/ml=1% ensures a strong protective action against influenza A and B viruses even on single administration if this is made at least 2–3 days up to 7 days before infection. Lower concentrations, e.g. 0.4%, are somewhat less effective.

Macroscopic and microscopic investigation of the lungs of mice to which a 1% solution of krestin was administered nasally 7 days before infection with A/HK 1/68, revealed much less pronounced pneumonic findings than in control animals treated with placebo.

A protective action similar to that obtained against the above A/Hong Kong 1/68 ($H_3N_2$) and B/AA 4/56 influenza viruses has also been observed against infections caused by other A ($H_3N_2$) strains, e.g. A/Vict. 3/75 and A/Port Chalmers 1/73 and especially A/Texas 1/77, by A ($H_2N_2$) strains, e.g. A/Singapore 1/57, by A ($H_1N_1$) strains, e.g. A/USSR 92/77, as well as against infections caused by influenza B viruses such as influenza B/Lee 40, and parainfluenza viruses such as parainfluenza 1/Sendai.

This action of krestin when applied nasally is superior to the prophylactic action of known antiviral substances, such as amantadine, against influenza viruses. Furthermore, krestin surprisingly affords also a very desirable protection in actual practice not only against influenza A viruses, but also against infections caused by influenza B viruses and other respiratory viruses. As against this, the oral or subcutaneous administration of krestin does not effect any significant protective action, as assays with mice infected in the manner indicated above with influenza A/Hong Kong 1/68 ($H_3N_2$) virus have shown.

As corresponding assays have demonstrated, the prevention treatment with krestin does not inhibit the formation of hemagglutinative serum antibodies against the virus. In assays with influenza virus infections of tissue cultures, krestin exhibits no inhibition of plaque formation and thus does not have antiviral properties analogous to those of e.g. amantadine. On the other hand, after mixing a suspension of A/HK 1/68 ($10 \times LD_{90}$ per 0.05 ml) with a 1% solution of krestin in vitro and allowing the mixture to stand for 30 minutes at 23° C., infectivity in mice on nasal application was neutralised, but there was found to be an increase in the hemagglutination inhibitory titre in the serum of mice treated with this mixture, and these animals were resistant to a re-infection with the $LD_{90}$ of the same virus.

Mice to which a vaccine against A/Vict. 3/75 (Begrivac ®, registered trade mark of Behringwerke, Marburg a.d. Lahn, Federal Republic of Germany) was administered subcutaneously with simultaneous nasal application of a 1% solution of krestin, were protected in the antibody-free latency period against infection by the same virus.

The local tolerance of aqueous solutions of krestin in low concentration is good. The twice daily application of the 1% aqueous solution to rabbits' eyes over 4 days resulted in no irritation—a fact which is all the more remarkable, as treatment intervals of several days are possible in practical application.

The nasal application of 0.1 ml of 1% or 3% solutions to guinea pigs three or five times weekly for 4 weeks resulted neither in allergic symptoms nor in the formation of serum antibodies, whereas animals treated in the same way with the known allergen ovalbumin died of anaphylaxis during or after the first 4-week treatment and had serum antibodies.

Krestin has no cytotoxic or cytostatic activity and during its clinical trials as tumour-inhibitor was also well tolerated when administered orally in higher doses of usually 1 g and more per day.

On the basis of the tumour-inhibiting action of krestin on oral administration, it was not to be expected that nasal application of krestin would exert the protective action observed in the practice of this invention against virus infections. The known oral administration of krestin in relatively high doses as tumour inhibitor in no way made obvious its nasal application for the same purpose and the protection of appropriate preparations.

The nasal preparations of this invention are, in particular, nasal drops, sprays, gels and ointments. These preparations contain the active ingredient in a prophylactically effective amount and concentration, i.e. one ensuring a protective action against virus infections of the above mentioned kind. Accordingly, the nasal preparations of the invention contain the active ingredient in a concentration suitable for administration of at least 2 mg of active ingredient each time. The upper limit is 4% (w/v) and the lower limit—because single administration can be made not only by once only nasal application, but also by repeated application once or more than once after the preparation has dried—is about 0.2% (w/v), correponding to 1 ml of a ready-for-use nasal preparation for the above minimum dose. Nasal drops have in particular a concentration between 1% and 2% and sprays a concentration between 0.2 and 1% of active ingredient. In both formulations the solvent is preferably water. The aqueous solutions optionally contain conventional pharmaceutically acceptable excipients for stabilising the active ingredient, as well as for buffering, preserving and/or lowering the surface tension, and they can be made isotonic in conventional manner, e.g. with sodium chloride or buffer solutions.

The invention relates in particular to spray bottles filled with the above solutions and to similar containers suitable for the intranasal application of such solutions.

The preparations of the present invention for the prevention of influenza A, influenza B, and other infections caused by other viruses of the respiratory tract, are preferably administered at intervals of 2 to 3 days or twice weekly. Instead of using the preparations of the invention for prolonged preventive treatment, e.g. right through the whole cold season, they can also be used only during part of the cold season when there is an obviously increased risk of infection. In addition, the preparations of the invention can also be used for bridging the latency period of vaccinations against influenza, i.e. simultaneously with or directly after vaccination, as the simultaneous nasal application with parenterally injected vaccine ensures protection in the antibody-free latency period without impairment of the antibody formation. The risk of catching an infection within the first two weeks after vaccination can thereby be reduced.

The above mentioned property of polysaccharides obtained from fungi, such as that of krestin, of neutralising the infectivity of virus suspensions, but not their ability to induce antibody formation, affords in addition the possibility of producing nasal preparations having vaccine activity for the prevention of infections caused by viruses of the respiratory tract. Such preparations for vaccination contain in aqueous medium, per 0.5 ml, i.e. in the amount of fluid which can comfortably be applied to each nostril by the single application of 0.25 ml, 2.5 to 10 mg, preferably 5 mg, corresponding to a concentration of 0.5 to 2%, preferably of 1%, of a nitrogen-containing polysaccharide obtained from fungi, such as krestin, in admixture with viruses of the respiratory tract of at least one strain, in an amount not exceeding that which becomes non-infectious as a result of the action of the nitrogen-containing polysaccharide at room to body temperature, especially at 20° to 25° C., and, if desired, with conventional excipients, e.g. preservatives. Such preparations are obtained by mixing an aqueous solution of a nitrogen-containing polysaccharide derived from fungi, especially krestin, of suitable concentration with an aqueous suspension of at least one strain of viruses of the respiratory tract. The concentrations of the aqueous solution of the polysaccharide and of the virus suspension are chosen such that the resultant mixture contains, per 0.5 ml, 2.5 to 10 mg of the polysaccharide, e.g. of krestin, and especially about 5 mg of krestin, and the viruses in an amount not exceeding that which can become non-infectious as a result of the action of the polysaccharide at room to body temperature. The duration of action at given or also varying temperature is determined by means of assays on mice for affording protection against infection with a corresponding sample mixture and is between about 15 minutes and about 120 minutes, depending on the sensitivity of the virus in question, in the preferred temperature range from 20°–25° C., most preferably at 23° C. The duration of action for A/Hong Kong 1/68 ($H_3N_2$) is shorter e.g. than for A/Texas 1/77. Then, if desired, excipients are added, e.g. preservatives such as sodium timerfonate [sodium p-(ethylmercurithio)-benzenesulfonate], and the preparation is stored in a refrigerator until use. The preparations of the invention are administered in a manner similar to that of non-vaccine preparations, but administration is made just once for a prolonged period of time, e.g. at the start of the cold season.

The following Examples illustrate a number of medicinal formulations, but without in any way restricting the scope of the invention thereto.

EXAMPLE 1

Nasal spray

A nasal spray with a 1% content of active ingredient is prepared by dissolving 10.0 g of krestin in 1 liter of distilled water and, if desired after the addition of 10 mg of sodium timerfonate [sodium p-(ethylmercurithio)-benzenesulfonate], filling 10 ml bottles with the solution. For prevention of influenza and other infections caused by viruses of the respiratory tract, each nostril is sprayed 2–3 times e.g. every second day or twice weekly from a full bottle, or, if necessary, more often from a partially empty bottle.

EXAMPLE 2

Nasal drops

Nasal drops containing 1% of active ingredient are prepared by dissolving 10.0 g of krestin in 1 liter of distilled water and, if desired after addition of 10 mg of sodium timerfonate, filling dropper bottles of 5 or 10 ml content provided with a stopper in the form of a pipette. In the same intervals as indicated in Example 1, 4–6 drops, corresponding to about 0.2 or 0.3 ml containing about 2–3 mg of active ingredient, are applied to each nostril.

EXAMPLE 3

Nasal preparation with vaccine action 100 ml of a nasal preparation with vaccine action which contains a 1% aqueous solution of krestin containing originally 700 infectious units (IU) of A/Texas influenza virus per 0.5 ml (usual vaccination dose), are prepared by mixing 80 ml of 1.25% solution of krestin in distilled water with 20 ml of a suspension of A/Texas 1/77 virus with a content of 7000 IU per ml and which has been purified in the usual manner. The mixture is kept at 23° C. for a period of time that was determined beforehand in assays on mice for affording protection against infection and in which a corresponding sample mixture proved to be non-infectious but induced a high antibody titre and resistence to re-infection, and which in the present instance was 60 minutes. Afterwards, if desired, a preservative is added, e.g. 1.0 mg of sodium timerfonate, and the preparation is stored in a refrigerator until use.

For influenza prevention by vaccination, preferably at the start of the cold season, 0.25 ml of the preparation is dropped into each nostril with a pipette.

What is claimed is:

1. A method of preventing infections caused by influenza A and B viruses of the respiratory tract, without inhibiting the formation of hemagglutinative serum antibodies against the virus, and without inhibiting plaque formation, which comprises applying into each nostril, up to seven days prior to infection, a preparation containing a prophylactically effective amount of krestin in a conventional medicinal formulation in order to protect the subject in the antibody-free latency period against infection by the same virus, to bridge the latency period of vaccination against influenza simultaneously with or directly after vaccination, or to ensure protection in the antibody-free latency period without impairment of the antibody formation.

2. The method of claim 1 wherein said preparation contains, as active ingredient, the nitrogen-containing polysaccharide krestin, in a prophylactically effective amount, in a conventional medicinal formulation for intranasal application selected from gels, ointments, and aqueous solutions.

3. The method of claim 1 wherein said preparation contains a pharmaceutically acceptable excipient of sodium timerfonate [sodium p-(ethylmercurithio)-benzenesulfonate].

4. The method of claim 1 wherein said preparation contains 0.2 to 4% krestin.

5. The method of claim 2 wherein said preparation contains 0.2 to 1% of krestin when said conventional medicinal formulation is an aqueous solution in the form of a spray.

6. The method of claim 2 wherein said preparation contains 1 to 2% of krestin when said conventional medicinal formulation is an aqueous solution in the form of drops.

7. A method of claim 1 wherein said preparation further comprises a virulent strain of said infectious virus of the respiratory tract in an amount not exceeding that which becomes non-infectious at room to body temperature as a result of the action of the amount of krestin in said preparation.

8. The method of claim 4 wherein said preparation further contains a pharmaceutically acceptable excipient of sodium timerfonate [sodium p-(ethylmercurithio)-benzenesulfonate].

* * * * *